(12) United States Patent
Lu et al.

(10) Patent No.: US 7,795,384 B2
(45) Date of Patent: Sep. 14, 2010

(54) FUSION PROTEIN SUITABLE FOR HIGH EFFICIENCY EXPRESSION AND THE PRODUCTION METHOD THEREOF

(75) Inventors: Yi Lu, Shanghai (CN); Xin Gao, Shanghai (CN); Dafu Cui, Shanghai (CN); Youshang Zhang, Shanghai (CN); Yangbin Huang, Shanghai (CN); Jiuru Sun, Shanghai (CN); Jiang Li, Shanghai (CN); Jian Fei, Shanghai (CN)

(73) Assignees: Shanghai Centre of Research & Development of New Drugs, Shanghai (CN); Shanghai Newsummit Biopharma Co., Ltd, Shanghai (CN); Shanghai Yizhong Biotechnology Co., Ltd, Shanghai (CN)

( * ) Notice: Subject to any disclaimer, the term of this patent is extended or adjusted under 35 U.S.C. 154(b) by 124 days.

(21) Appl. No.: 10/559,059

(22) PCT Filed: Jun. 3, 2003

(86) PCT No.: PCT/CN03/00426

§ 371 (c)(1),
(2), (4) Date: Jan. 30, 2007

(87) PCT Pub. No.: WO2004/106525

PCT Pub. Date: Dec. 9, 2004

(65) Prior Publication Data

US 2008/0045695 A1 Feb. 21, 2008

(51) Int. Cl.
*A61K 38/28* (2006.01)
*A61K 38/16* (2006.01)
(52) U.S. Cl. ..................... 530/303; 530/324
(58) Field of Classification Search ........... None
See application file for complete search history.

(56) References Cited

U.S. PATENT DOCUMENTS 3,953,418 A * 4/1976 Yanaihara et al. ........... 530/303
5,028,524 A * 7/1991 Fujisawa et al. ............ 435/5

FOREIGN PATENT DOCUMENTS

| EP | 0 281 418 B1 | | 1/1995 |
| EP | 0 453 969 B1 | | 9/1996 |
| WO | 93/10152 | | 5/1993 |
| WO | 97/11186 | | 3/1997 |
| WO | WO 99/07735 | * | 2/1999 |
| WO | 00/17336 | | 3/2000 |
| WO | WO 2004/106525 | * | 12/2004 |

OTHER PUBLICATIONS

Ghosh et al., 1996, Gene v176 pp. 249-255.*
Sidorkiewicz et al ("Expression and characterization of the multiplied, recombinant preS1 antigen of hepatitis B virus" Arch Virol (1995) 140:1935-1944).*

* cited by examiner

*Primary Examiner*—Anish Gupta
*Assistant Examiner*—Ronald T Niebauer
(74) *Attorney, Agent, or Firm*—Merchant & Gould P.C.

(57) ABSTRACT

The present invention provides a novel fusion protein suitable for high expression and the production method thereof. The structure of the fusion protein is A-C1-K-(B-C2-K)n-D, wherein A is the upstream peptide; each of C1 and C2 is independently short peptides having 20-40 amino acids in length and containing no Lys in sequence; K is Lys; B is a linker; D is a downstream peptide; n is an integer of 3-30. The fusion protein is expressed with high efficiency and stability in host cells. The purification and enzymatic cleavage technology of the expression product is simple, which is able to produce a short peptide with high efficiency, and has very high value of industrialization.

3 Claims, 4 Drawing Sheets a b c d e f g e a b c d

SEQUENCE LISTING

```
<160> NUMBER OF SEQ ID NOS: 8

<210> SEQ ID NO 1
<211> LENGTH: 1056
<212> TYPE: DNA
<213> ORGANISM: Artificial
<220> FEATURE:
<221> NAME/KEY: misc_feature
<223> OTHER INFORMATION: DNA encoding fusion

<400> SEQUENCE: 1
gaggctgaag cttacgtaga attcatgcat catcatcatc atcatagatc taaggaagct      60
gaagatttgc aagttggtca agttgaattg ggtggtgggc ccggtgctgg ttctttgcaa     120
ccattggctt tggaaggttc tttgcaaaag gctggatcta aggaagctga agatttgcaa     180
gttggtcaag ttgaattggg tggtgggccc ggtgctggtt ctttgcaacc attggctttg     240
gaaggttctt tgcaaaaggc tggatctaag gaagctgaag atttgcaagt tggtcaagtt     300
gaattgggtg gtgggcccgg tgctggttct tgcaaccat tggctttgga aggttctttg     360
caaaaggctg gatctaagga agctgaagat ttgcaagttg gtcaagttga attgggtggt     420
gggcccggtg ctggttcttt gcaaccattg gctttggaag ttctttgca aaaggctgga     480
```

```
tctaaggaag ctgaagattt gcaagttggt caagttgaat tgggtggtgg gcccggtgct    540
ggttctttgc aaccattggc tttggaaggt tctttgcaaa aggctggatc taaggaagct    600
gaagatttgc aagttggtca agttgaattg ggtggtgggc ccggtgctgg ttctttgcaa    660
ccattggctt tggaaggttc tttgcaaaag gctggatcta aggaagctga agatttgcaa    720
gttggtcaag ttgaattggg tggtgggccc ggtgctggtt ctttgcaacc attggctttg    780
gaaggttctt tgcaaaaggc tggatctaag gaagctgaag atttgcaagt tggtcaagtt    840
gaattgggtg gtgggcccgg tgctggttct ttgcaaccat ggctttggaa ggttctttg    900 caaaaggctg gatctaagga agctgaagat ttgcaagttg gtcaagttga attgggtggt    960
gggcccggtg ctggttcttt gcaaccattg gctttggaag ttctttgca aaaggctgga   1020 tccctgaatt ccctagggcg ccgcgaatt aattcg                              1056
```

<210> SEQ ID NO 2
<211> LENGTH: 344
<212> TYPE: PRT
<213> ORGANISM: Artificial
<220> FEATURE:
<221> NAME/KEY: misc_feature
<223> OTHER INFORMATION: fusion protein

<400> SEQUENCE: 2

```
Met His His His His His His Arg Ser Lys Glu Ala Glu Asp Leu Gln
1               5                   10                  15

Val Gly Gln Val Glu Leu Gly Gly Gly Pro Gly Ala Gly Ser Leu Gln
            20                  25                  30

Pro Leu Ala Leu Glu Gly Ser Leu Gln Lys Ala Gly Ser Lys Glu Ala
        35                  40                  45

Glu Asp Leu Gln Val Gly Gln Val Glu Leu Gly Gly Gly Pro Gly Ala
    50                  55                  60

Gly Ser Leu Gln Pro Leu Ala Leu Glu Gly Ser Leu Gln Lys Ala Gly
65                  70                  75                  80

Ser Lys Glu Ala Glu Asp Leu Gln Val Gly Gln Val Glu Leu Gly Gly
                85                  90                  95

Gly Pro Gly Ala Gly Ser Leu Gln Pro Leu Ala Leu Glu Gly Ser Leu
            100                 105                 110

Gln Lys Ala Gly Ser Lys Glu Ala Glu Asp Leu Gln Val Gly Gln Val
        115                 120                 125

Glu Leu Gly Gly Gly Pro Gly Ala Gly Ser Leu Gln Pro Leu Ala Leu
    130                 135                 140

Glu Gly Ser Leu Gln Lys Ala Gly Ser Lys Glu Ala Glu Asp Leu Gln
145                 150                 155                 160

Val Gly Gln Val Glu Leu Gly Gly Gly Pro Gly Ala Gly Ser Leu Gln
                165                 170                 175

Pro Leu Ala Leu Glu Gly Ser Leu Gln Lys Ala Gly Ser Lys Glu Ala
            180                 185                 190

Glu Asp Leu Gln Val Gly Gln Val Glu Leu Gly Gly Gly Pro Gly Ala
        195                 200                 205

Gly Ser Leu Gln Pro Leu Ala Leu Glu Gly Ser Leu Gln Lys Ala Gly
    210                 215                 220

Ser Lys Glu Ala Glu Asp Leu Gln Val Gly Gln Val Glu Leu Gly Gly
225                 230                 235                 240

Gly Pro Gly Ala Gly Ser Leu Gln Pro Leu Ala Leu Glu Gly Ser Leu
                245                 250                 255
```

```
Gln Lys Ala Gly Ser Lys Glu Ala Glu Asp Leu Gln Val Gly Gln Val
            260                 265                 270

Glu Leu Gly Gly Gly Pro Gly Ala Gly Ser Leu Gln Pro Leu Ala Leu
            275                 280                 285

Glu Gly Ser Leu Gln Lys Ala Gly Ser Lys Glu Ala Glu Asp Leu Gln
            290                 295                 300

Val Gly Gln Val Glu Leu Gly Gly Gly Pro Gly Ala Gly Ser Leu Gln
305                 310                 315                 320

Pro Leu Ala Leu Glu Gly Ser Leu Gln Lys Ala Gly Ser Leu Asn Ser
            325                 330                 335

Leu Gly Arg Pro Arg Ile Asn Ser
            340

<210> SEQ ID NO 3
<211> LENGTH: 445
<212> TYPE: PRT
<213> ORGANISM: Artificial
<220> FEATURE:
<221> NAME/KEY: misc_feature
<223> OTHER INFORMATION: fusion protein

<400> SEQUENCE: 3

Met His His His His His Arg Ser Lys Glu Ala Glu Asp Leu Gln
1               5                   10                  15

Val Gly Gln Val Glu Leu Gly Gly Gly Pro Gly Ala Gly Ser Leu Gln
            20                  25                  30

Pro Leu Ala Leu Glu Gly Ser Leu Gln Lys Ala Gly Ser Lys Glu Ala
            35                  40                  45

Glu Asp Leu Gln Val Gly Gln Val Glu Leu Gly Gly Gly Pro Gly Ala
            50                  55                  60

Gly Ser Leu Gln Pro Leu Ala Leu Glu Gly Ser Leu Gln Lys Ala Gly
65                  70                  75                  80

Ser Lys Glu Ala Glu Asp Leu Gln Val Gly Gln Val Glu Leu Gly Gly
            85                  90                  95

Gly Pro Gly Ala Gly Ser Leu Gln Pro Leu Ala Leu Glu Gly Ser Leu
            100                 105                 110

Gln Lys Ala Gly Ser Lys Glu Ala Glu Asp Leu Gln Val Gly Gln Val
            115                 120                 125

Glu Leu Gly Gly Gly Pro Gly Ala Gly Ser Leu Gln Pro Leu Ala Leu
            130                 135                 140

Glu Gly Ser Leu Gln Lys Ala Gly Ser Lys Glu Ala Glu Asp Leu Gln
145                 150                 155                 160

Val Gly Gln Val Glu Leu Gly Gly Gly Pro Gly Ala Gly Ser Leu Gln
            165                 170                 175

Pro Leu Ala Leu Glu Gly Ser Leu Gln Lys Ala Gly Ser Lys Glu Ala
            180                 185                 190

Glu Asp Leu Gln Val Gly Gln Val Glu Leu Gly Gly Gly Pro Gly Ala
            195                 200                 205

Gly Ser Leu Gln Pro Leu Ala Leu Glu Gly Ser Leu Gln Lys Ala Gly
            210                 215                 220

Ser Lys Glu Ala Glu Asp Leu Gln Val Gly Gln Val Glu Leu Gly Gly
225                 230                 235                 240

Gly Pro Gly Ala Gly Ser Leu Gln Pro Leu Ala Leu Glu Gly Ser Leu
            245                 250                 255

Gln Lys Ala Gly Ser Lys Glu Ala Glu Asp Leu Gln Val Gly Gln Val
```

-continued

```
                260                 265                 270
Glu Leu Gly Gly Gly Pro Gly Ala Gly Ser Leu Gln Pro Leu Ala Leu
            275                 280                 285
Glu Gly Ser Leu Gln Lys Ala Gly Ser Lys Glu Ala Glu Asp Leu Gln
            290                 295                 300
Val Gly Gln Val Glu Leu Gly Gly Pro Gly Ala Gly Ser Leu Gln
305                 310                 315                 320
Pro Leu Ala Leu Glu Gly Ser Leu Gln Lys Ala Gly Ser Lys Glu Ala
                325                 330                 335
Glu Asp Leu Gln Val Gly Gln Val Glu Leu Gly Gly Pro Gly Ala
            340                 345                 350
Gly Ser Leu Gln Pro Leu Ala Leu Glu Gly Ser Leu Gln Lys Ala Gly
            355                 360                 365
Ser Lys Glu Ala Glu Asp Leu Gln Val Gly Gln Val Glu Leu Gly Gly
            370                 375                 380
Gly Pro Gly Ala Gly Ser Leu Gln Pro Leu Ala Leu Glu Gly Ser Leu
385                 390                 395                 400
Gln Lys Ala Gly Ser Lys Glu Ala Glu Asp Leu Gln Val Gly Gln Val
                405                 410                 415
Glu Leu Gly Gly Gly Pro Gly Ala Gly Ser Leu Gln Pro Leu Ala Leu
            420                 425                 430
Glu Gly Ser Leu Gln Lys Ala Gly Ser Leu Asn Ser Pro
            435                 440                 445

<210> SEQ ID NO 4
<211> LENGTH: 10
<212> TYPE: PRT
<213> ORGANISM: Artificial
<220> FEATURE:
<221> NAME/KEY: MISC_FEATURE
<222> LOCATION: (1)..(10)
<223> OTHER INFORMATION: upstream peptide

<400> SEQUENCE: 4

Met His His His His His His Arg Ser Lys
1               5                   10

<210> SEQ ID NO 5
<211> LENGTH: 4
<212> TYPE: PRT
<213> ORGANISM: Artificial
<220> FEATURE:
<221> NAME/KEY: MISC_FEATURE
<222> LOCATION: (1)..(4)
<223> OTHER INFORMATION: linker

<400> SEQUENCE: 5

Ala Gly Ser Lys
1

<210> SEQ ID NO 6
<211> LENGTH: 14
<212> TYPE: PRT
<213> ORGANISM: Artificial
<220> FEATURE:
<221> NAME/KEY: MISC_FEATURE
<222> LOCATION: (1)..(14)
<223> OTHER INFORMATION: downstream peptide

<400> SEQUENCE: 6

Ala Gly Ser Leu Asn Ser Leu Gly Arg Pro Arg Ile Asn Ser
1               5                   10
```

```
<210> SEQ ID NO 7
<211> LENGTH: 7
<212> TYPE: PRT
<213> ORGANISM: Artificial
<220> FEATURE:
<221> NAME/KEY: MISC_FEATURE
<222> LOCATION: (1)..(7)
<223> OTHER INFORMATION: downstream peptide

<400> SEQUENCE: 7

Ala Gly Ser Leu Asn Ser Pro
1               5

<210> SEQ ID NO 8
<211> LENGTH: 71
<212> TYPE: PRT
<213> ORGANISM: Artificial
<220> FEATURE:
<221> NAME/KEY: MISC_FEATURE
<223> OTHER INFORMATION: fusion protein

<400> SEQUENCE: 8

His His His His His His Lys Glu Ala Glu Asp Leu Gln Val Gly Gln
1               5                   10                  15

Val Glu Leu Gly Gly Gly Pro Gly Ala Gly Ser Leu Gln Pro Leu Ala
            20                  25                  30

Leu Glu Gly Ser Leu Gln Lys Glu Ala Glu Asp Leu Gln Val Gly Gln
        35                  40                  45

Val Glu Leu Gly Gly Gly Pro Gly Ala Gly Ser Leu Gln Pro Leu Ala
    50                  55                  60

Leu Glu Gly Ser Leu Gln Lys
65                  70
```

FUSION PROTEIN SUITABLE FOR HIGH EFFICIENCY EXPRESSION AND THE PRODUCTION METHOD THEREOF

TECHNICAL FIELD

The present invention relates to the field of genetic engineering. More specifically, the present invention relates to a fusion protein suitable for high efficiency expression and the production method thereof. This fusion protein is particularly suitable for high effectively producing short peptides without lysine residues.

BACKGROUND ART

Pichia *pastoris* and *E. coli* expression systems are suitable to express products with a molecular weight of about 5 to 200 KD. Both of these two systems can not express short peptides with a molecular weight of about 1 to 5 KD, or even if some peptides can be expressed, the expression levels are relatively low in general.

In addition, there is another problem for the expression of short peptides with low molecular weights, i.e., it is difficult to detect the products. The normal molecular weights of standards in the conventional SDS-PAGE are between the range of 14-65 KD. Short peptides are out of the detectable range (the highest concentration of gels used in SDS-PAGE is about 20%, where the detectable linear range of the molecular weight is 10 to 40 KD); short peptides are, therefore, prone to run out of the gel, leading to imprecise results.

Short peptides can be used to treat a lot of common diseases. For example, diabetic nephropathy (DN) is one of the chronic common complications of diabetes, and has become a major cause for end-stage renal disease (ESRD). About 35% type I diabetic patients and 15% type II diabetic patients will finally develop diabetic nephropathy. The proinsulin C-peptide is a peptide secreted by the pancreatic beta cells, which consists of 31 amino acid residues. It has been demonstrated that the proinsulin C-peptide can ameliorate long-term diabetic complications (including diabetic nephropathy). Furthermore, it has also been shown that the C-peptide, employed alone or together with insulin, can reduce the mesentery expansion resulted from extracellular matrix accumulation around renal glomeruli. This function of the C-peptide may explain the major mechanism for treating diabetic microangiopathy, including diabetic nephropathy. Accordingly, under the circumstance that insulin still moderately regulates carbohydrate metabolism, a combination treatment with the C-peptide can significantly ameliorate the onset and development of diabetic nephropathy. Since there are millions of diabetic patients, short peptide drugs such as the C-peptide are in great demand.

At present, short peptide drugs used in the international market are mostly produced by chemical synthesis with high cost. Therefore, there is an urgent need for genetic engineering methods to produce short peptides on a large scale and with simple process and low cost.

Constructing multiple copies is an efficient means to increase the expression level of short peptides. Multicopy genes can be constructed to express fusion proteins with high molecular weight, so as to achieve high efficient expression and facilitate detection.

For multicopy fusion proteins with high expression efficiency and the genes encoding the same, the following problems must be addressed: (a) selection of the target gene (or target protein); (b) length (i.e., the number of copies); (c) ligation linker, said ligation includes the ligation of fusion protein with the expression plasmid, the ligation between target protein monomers, and the selection of signal peptides, etc.; and (d). enzymatic digestion after expression. Any inappropriate selection would affect the expression level, or even prevent the fusion protein from expressing.

One common strategy is to fuse the multicopy short peptide with another peptide having higher molecular weight (about 10-20 KD) to ensure the stable presence of the fusion protein in host cells. The disadvantage of this method, however, is that the desired short peptide only accounts for a small proportion in the fusion protein, thus lowering the efficiency. Furthermore, fusion proteins formed with GST or other proteins add to the processing complexity, which requires the step of enzymatic digestion and purification.

Another ideal strategy is to insert some short upstream and downstream sequences at the upstream or downstream of the multicopy short peptide, which significantly increase the proportion of the short peptide in the fusion protein. Yet at present, most of the fusion proteins constructed by this method are unstable and can not yield expression products in a large amount.

Accordingly, there is an urgent need in the art to develop a method for expressing multicopy short peptides high effectively and stably.

SUMMARY OF INVENTION

The object of the present invention is to provide a method for expressing multicopy short peptides in a manner of high efficiency and stable expression level.

Another object of the invention is to provide the related fusion proteins, vectors and host cells.

In one aspect, the present invention provides a fusion protein of the following structure:

A-C1-K-(B-C2-K)n-D

Wherein, A is MHHHHHHRSK (SEQ ID NO:4), each of C1 and C2 is independently short peptide having 20-40 amino acids in length and containing no Lys in sequence;

K is Lys;

B is AGSK (SEQ ID NO:5);

D is a downstream peptide of 3-15 amino acids in length and the first three amino acids thereof are AGS; and n is an integer between 3-30.

In another preferred example, C1 and C2 are identical, more preferably, both C1 and C2 are the proinsulin C-peptide.

In another preferred example, C1 and C2 are different and their length difference is 8-10 amino acids.

In another preferred example, C1 and C2 are selected from the proinsulin C-peptide, α-ANP, or pre-S1 antigen peptide for Hepatitis B.

In another preferred example, said fusion protein has the amino acid sequence set forth in SEQ ID NO:2 or 3.

In the second aspect of the present invention, a DNA molecule is provided, which encodes the above-mentioned fusion protein of invention.

In the third aspect of the present invention, an expression vector is provided, which contains the above-mentioned DNA molecule of the present invention.

In the fourth aspect of the present invention, a host cell is provided, which contains the expression vector according to the present invention or the aforementioned DNA molecule integrated into its genome. More preferably, said host cell is Pichia *pastoris* or *E. coli*.

In the fifth aspect of the present invention, a method for the production of fusion proteins is provided, comprising:

(a) culturing the host cells according to the invention for the expression of the fusion protein;

(b) isolating the fusion protein.

In the sixth aspect of the present invention, a method for the production of short peptides is provided, comprising:

(c) digesting the fusion protein according to the present invention with trypsinase and carboxypeptidase B, resulting in short peptides C1 and C2; and (d) isolating short peptides C1 and C2.

More preferably, C1 and C2 are identical in the above-mentioned methods, and both of them are the proinsulin C-peptide.

MODE FOR CARRYING OUT THE INVENTION

Figure 1:
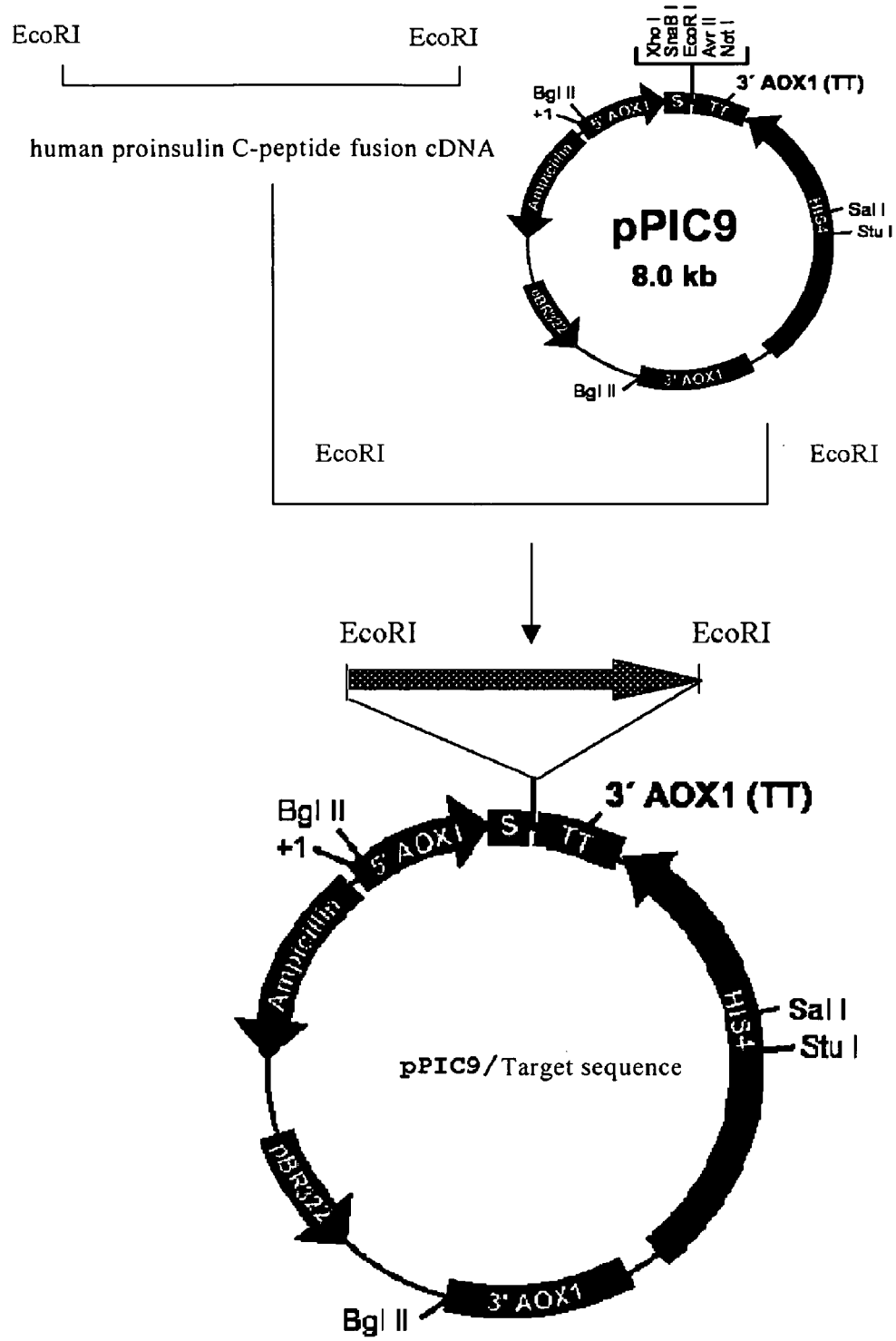
FIG. 1 shows the construction of the plasmid for the expression of fusion protein of human proinsulin C-peptide in Pichia *pastoris*.

Through extensive and intensive investigation, the inventors of the present invention have found that the A-C1-K-(B-C2-K)n-D structure, which is formed by inserting the upstream peptide MHHHHHHRSK (SEQ ID NO:4) to the upstream of multicopy short peptide, has several advantages, thereby make it possible to express fusion proteins with high efficiency in Pichia *pastoris* or *E. coli*. On this basis, the inventors completed the present invention.

Structure of the Fusion Protein

The fusion protein of invention is the non-native form. Various components of the entire fusion protein are linearly linked, and generally no disulfide bonds exist in structure. Therefore, the fusion protein is linearly structured without dimensional folding, thus prone to be digested by various proteases.

(i) Upstream Peptide

In the fusion protein of the invention with the general formula of A-C1-K-(B-C2-K)n-D, the key element for stable and high efficient expression is the upstream peptide A, i.e., MHHHHHHRSK (SEQ ID NO:4). This component not only enables the expression of the fusion protein comprising multicopy element C1-K-(B-C2K)n, but also stabilizes the fusion protein in the host cells. In addition, the upstream element is very short, therefore the target protein accounts for a high proportion in the fusion protein.

(ii) Short Peptides

In the fusion protein of invention, each of C1 and C2 is independently a short peptide with 10-40 amino acids in length. Since enzymes such as trypsinase, carboxypeptidase B directed to basic amino acids (such as Lys) will be utilized to digest the fusion protein into short peptides, C1 and C2 must not contain basic amino acids (such as Lys and Arg). Suitable examples include proinsulin C-peptide (31aa), a-ANP (28aa), pre-S1 antigen peptide of Hepatitis B (28aa), and the like.

C1 and C2 may be identical or different. When the both are identical, upon digestion the fusion protein gives the desired short peptides of 20-40 amino acids, linker of 4-15 amino acids, upstream peptide and downstream peptide. Due to their different lengths, it is convenient to obtain short peptides through purification. In a preferred embodiment, both of C1 and C2 are the proinsulin C-peptide.

When C1 and C2 are different, a difference of 8-10 amino acids in length may be proper, so as to separate C1 and C2 after digestion. If C1 and C2 are two short peptides, which can be used in combination, then it is not necessary to separate them. In this case, C1 and C2 can be of the same length.

In the fusion protein of invention, n is an integer between 3-30, preferably between 5-25, more preferably between 8-15. In this case, the molecular weight of the fusion protein is about 6-60 KD, suitable to be expressed in Pichia *pastoris* and *E. coli* expression systems. For other suitable expression systems, the upper limit for n may exceed 20, for example, 25, 30, 35, 40 or higher.

(iii) Linker

In the fusion protein of the invention, B is a linker. In general, the linker consists of 4-10 amino acids. The shorter the linker is, the higher proportion the short peptide accounts for in the fusion protein, and the easier to separate due to the larger difference between the lengths of the short peptides and the linker. Accordingly, short linker is more suitable for the present invention. Furthermore, the carboxyl terminal of the linker should be Lys or Arg. A preferred linker is AGSK (SEQ ID NO:5).

(iv) Downstream Peptide

In the fusion protein of invention, D is a downstream peptide that acts to provide the digestion site for carboxypeptidase in conjunction with Lys upstream of the downstream peptide. In certain circumstances, the encoding sequence of the downstream peptide can also provide restriction sites for cloning.

The downstream peptide may or may not exist. When B is AGSK (SEQ ID NO:5), it is proper that D is a downstream peptide with 3-15 amino acids in which the first three amino acids is AGS. Suitable examples include (but are not limited to): AGSLNSLGRPRINS (SEQ ID NO:6) and AGSLNSP (SEQ ID NO:7).

Construction of the Fusion Gene, Vectors and Host Cells

In the present invention, once the sequence of the fusion protein is determined, then the fusion gene, vectors and host cells can be constructed by routine methods. There are no specific limitations for the vectors and host cells suitable for the present invention.

Typically, the encoding DNA is designed at first according to the amino acid sequence of the fusion protein in the present invention. Preferably, the codon can be optimized according to the selected host cells, such as Pichia pastoris or E. coli.

Then, one may select an expression vector, such as pPIC9 or pPIC9K of Pichia pastoris system, or pET30(a) of E. coli system and design enzymatic digestion sites according to the selected vector.

Next, one may synthesize the designed encoding sequence for the fusion protein, and clone it into the expression vector after enzymatic digestion.

Finally, one may transfect Pichia pastoris or transform E. coli with the expression vector by routine methods. Host cells with high efficient expression can be obtained through methods such as resistance screening.

Production and Purification of the Fusion Protein

Conventional methods and conditions can be employed to culture the transformed host cells to express the fusion protein. Conventional purification methods can be used for separation and purification (for example, salting out, centrifugation, molecular sieve chromatography, adsorption chromatography, ion-exchange chromatography, HPLC and so on).

For example, suitable mediums for the culture and expression of Pichia pastoris include, but are not limited to, the following:

| | | |
|---|---|---|
| YPD plate | Yeast Extracts | 1% |
| | Peptone | 2% |
| | Glucose | 2% |
| | Agar | 1% |
| BMGY Medium | Yeast Extracts | 1% |
| | Peptone | 2% |
| | Potassium phosphate buffer, pH 6.0 | 100 mM |
| | YNB | 1.34% |
| | Biotin | $(4 \times 10^{-5})\%$ |
| | Glycerol | 1% |
| MM Medium | YNB | 1.34% |
| | Biotin | $(4 \times 10^{-5})\%$ |
| | Methanol | 0.5% |

A preferred condition for culture in a shake flask is as follows: picking out a mono-colony on the YPD plate, using BMGY as the shake flask medium to allow the P. pastoris grow till $OD_{600}=2$-20, and adding 1% methanol to induce expression. After 24 hours of induction, the concentration of the target protein in the supernatant of the medium can be up to 50-200 mg/L.

For pilot-plant and large-scale production, the expression conditions for P. Pastoris engineering cell should be optimized. Pilot-plant fermentation means fermenter fermentation. The preferred production conditions are as follows:

1. As to the selection of the medium, low salt medium can be selected for fermenter fermentation, or some modifications can be made on the basis of the low salt medium while maintaining similar ion components.

| | | |
|---|---|---|
| Low salt fermentation medium | $H_3PO_4$ (85% storage concentration) | 26.7 ml/L |
| | $CaSO_4 \cdot 2H_2O$ | 0.93 g/L |
| | $K_2SO_4$ | 18.2 g/L |
| | $MgSO_4$ | 7.27 g/L |
| | KOH (solid) | 4.13 g/L |
| | Sodium citric acid·$2H_2O$ | 1.47 g/L |
| | $PTM_1$ | 2 ml/L |
| | Glycerol | 4%(w/v) |
| $PTM_1$ | $CuSO_4 \cdot 5H_2O$ | 6 g/L |
| | KI | 0.08 g/L |
| | $MnSO_4 \cdot H_2O$ | 3 g/L |
| | Sodium molybdate | 0.2 g/L |
| | Boric acid | 0.02 g/L |
| | $CaSO_4 \cdot 2H_2O$ | 0.5 g/L |
| | $ZnCl_2$ | 20 g/L |
| | Cobalt chloride | 0.5 g/L |
| | $FeSO_4$ | 65 g/L |
| | Biotin | 0.2 g/L |
| | $H_2SO_4$ | 5 ml/L |

2. As to the temperature control, fermentation and induction temperature should be kept at 25-31° C.

3. For pH in the induction period, pH should be maintained at 4-8 during the induction period, preferably, at 5-7.

4. For dissolved oxygen (DO), DO should be maintained at 20-90%, which can be controlled by introducing oxygen/air mixture gas.

5. For flowing feed of the supplement, appropriate supplement includes glycogen, such as glycerol, methanol and glucose, which is supplemented alone or in mixture.

6. As to the amount of $PTM_1$ (trace element solution), the amount of $PTM_1$ at the initial stage is 1-4 ml/L of the medium, while during the supplemental period, the amount is 2-20 ml/L of the supplement.

7. As to the methanol concentration for the induction period, conventional induction concentration is applicable to the present invention, and methanol concentration is commonly controlled at 0.5-2%.

8. The induction time is typically 10-100 hours, preferably 20-60 hours.

Preparation of Short Peptide Monomers

The fusion protein of invention is a good starting material for the preparation of short peptide monomers. Short peptide monomers may be obtained through enzymatic digestion and separation of the fusion protein.

Typically, the useful enzymes are those directed at basic amino acids, for example, trypsinase, carboxypeptidase B, etc. Two-step digestion method can be used, i.e., firstly short peptides with K (such as C1K or C2K) are formed by digestion, and then K is removed to produce short peptide monomers. One-step digestion method may also be used, which involves digestion with the mixture of two enzymes to directly produce short peptide monomers.

There are no specific limitations for the condition of enzymatic digestion, and the conventional conditions therefore may be adopted. For example, The concentration of the fusion protein is 0.1-100 mg/ml, preferably 1-50 mg/ml;

The ratio of enzyme to protein is 1:10-1:5000, preferably 1:50-1:500;

The temperature for enzymatic digestion is 15-35° C., preferably 20-30° C.;

The pH for enzymatic digestion is 5.0-10.0, preferably 6.0-9.0;

The buffer used are phosphate buffer, acetate buffer, Tris, or carbonate buffer, the concentration of which are 10-200 mM;

The time for enzymatic digestion is 1-50 hrs, preferably 1-10 hrs.

Conventional techniques (for example, cation-exchange chromatography, anion exchange chromatography, gel filtration chromatography, hydrophobic chromatography, reversed phase chromatography, affinity chromatography, etc) may be applied to the digested mixture to purify the short peptide monomers. It is preferable to subject the digested samples to ion-exchange chromatography, hydrophobic chromatography and reversed phase chromatography.

The resultant short peptide monomers may be made into the corresponding preparation by conventional methods. For example, if the short peptide is the proinsulin C-peptide, appropriate supplements may be added to the purified original stock solution, such as the stabilizer of 1-10% mannitol (or sucrose, lactose, etc.). Protective agents, such as surfactant and antioxidant, and appropriate buffer can also be added. The resultant product is subpackaged to produce the preparation of the aqueous solution of C-peptide, or lyophilized to prepare the powder of C-peptide for injection.

The main advantages of the present invention includes:
i. high level and stable expression;
ii. high output of short peptides (such as human proinsulin C-peptide);
iii. simple methods of preparation and purification, leading to low costs;
iv. When expressed in eukaryotic expression system -Pichia pastoris system, the target protein has a higher homology to that of mammals, thus producing fewer toxic and side effects.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1

Pichia pastoris Expressing the Fusion Protein of Human Proinsulin C-Peptide—Construction of Engineered Cells In this example, C1=C2=the proinsulin C-peptide, n=8.
1. Full length amino acid sequence of the fusion protein:

(SEQ ID NO:2)
MHHHHHHRSKEAEDLQVGQVELGGGPGAGSLQPLALEGSLQKAGSKEAE

DLQVGQVELGGGPGAGSLQPLALEGSLQKAGSKEAEDLQVGQVELGGGPG

AGSLQPLALEGSLQKAGSKEAEDLQVGQVELGGGPGAGSLQPLALEGSLQ

KAGSKEAEDLQVGQVELGGGPGAGSLQPLALEGSLQKAGSKEAEDLQVGQ

VELGGGPGAGSLQPLALEGSLQKAGSKEAEDLQVGQVELGGGPGAGSLQP

LALEGSLQKAGSKEAEDLQVGQVELGGGPGAGSLQPLALEGSLQKAGSK

EAEDLQVGQVELGGGPGAGSLQPLALEGSLQKAGSLNSLGRPRINS

2. Construction

The full length sequence of the gene for the fusion protein was synthesized according to SEQ ID NO:2 and the codon bias of Pichia pastoris (adding EcoRI sites at both sides), and shown in SEQ ID NO:1. The ORF is position 25-1056, immediately downstream of which was the stop codon.

The gene were cloned into pUC19, verified by sequencing, digested with EcoRI and then cloned into the plasmid pPIC9 (Invitrogen), which had also been digested with EcoRI. Then, Pichia pastoris (P. Pastoris) GS115 (Invitrogen) was transformed with the plasmid, thereby integrating into the yeast's' chromosomes. The transformed cells with multicopy gene incorporated therein were picked out through screening with dot hybridization, so that the engineering cells was picked out (FIG. 1). The engineering cells might utilize the methanol rapidly (Mut$^+$) or slowly (Mut$^s$).

3. Expression

Figure 2:
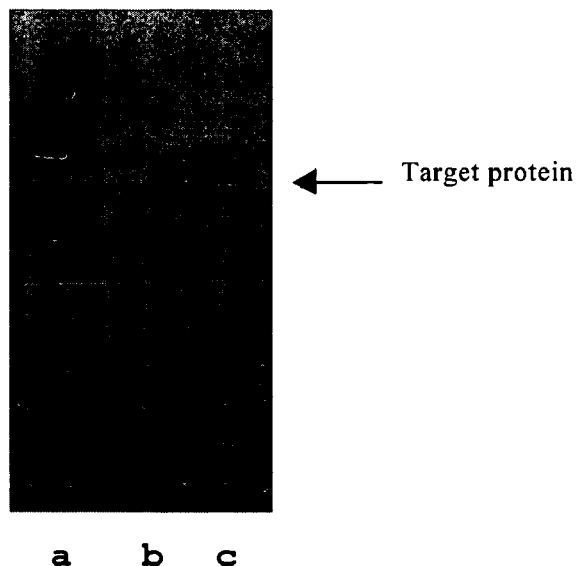
FIG. 2 shows the SDS-PAGE electrophoresis analysis of fusion protein of human proinsulin C-peptide expressed by Pichia *pastoris*. Lane a: molecular weight standards (from top to bottom, molecular weights are 96 KD, 66 KD, 43 KD, 31 KD, 20.1 KD, and 14.4 KD); b: blank control; c: supernatant of the medium (the C-peptide fusion protein).

Strains with high efficiency expression were picked out by screening (the integrated copy number is examined to be ≧220). Shake flask test with BMGY medium demonstrated that, after 24 hours of induction, the target protein accounted for over 50% of the total proteins in the supernatant, with the expression level over 100 ug/ml (FIG. 2). According to the rate of methanol consumption, this engineering cell was confirmed to be Mut$^+$ strain.

Example 2

Pichia pastoris Expressing the Fusion Protein of Human Proinsulin C-Peptide—Construction of Engineered Cells In this example, C1=C2=the proinsulin C-peptide, n=11.
The second fusion protein was constructed by using the same method described in example 1, except for the different downstream peptide D.

(SEQ ID NO:3)
MHHHHHHRSKEAEDLQVGQVELGGGPGAGSLQPLALEGSLQKAGSKEAED

LQVGQVELGGGPGAGSLQPLALEGSLQKAGSKEAEDLQVGQVELGGGPGA

GSLQPLALEGSLQKAGSKEAEDLQVGQVELGGGPGAGSLQPLALEGSLQK

AGSKEAEDLQVGQVELGGGPGAGSLQPLALEGSLQKAGSKEAEDLQVGQV

ELGGGPGAGSLQPLALEGSLQKAGSKEAEDLQVGQVELGGGPGAGSLQPL

ALEGSLQKAGSKEAEDLQVGQVELGGGPGAGSLQPLALEGSLQKAGSKEA

EDLQVGQVELGGGPGAGSLQPLALEGSLQKAGSKEAEDLQVGQVELGGGP

GAGSLQPLALEGSLQKAGSKEAEDLQVGQVELGGGPGAGSLQPLALEGSL

QKAGSKEAEDLQVGQVELGGGPGAGSLQPLALEGSLQKAGSLNSP

Strains with high efficiency expression were picked out by screening (the integrated copy number is examined to be ≧220). Shake flask test with BMGY medium demonstrated that, after 24 hours of induction, the target protein accounted for over 50% of the total proteins in the supernatant, with the expression level over 100 ug/ml. According to the rate of methanol consumption, this engineering cell was confirmed to be Mut$^+$ strain.

Example 3

Pichia pastoris Expressing the Fusion Protein of Human Proinsulin C-Peptide—Construction of Engineered Cells In this example, several protocols of constructing Pichia pastoris engineering cells for the expression of fusion protein of human proinsulin C-peptide were compared.
Protocol 1 was Example 1.

The structure of the fusion protein in protocol 2 was HHH-HHHKEAEDLQVGQVELGGGPGAGSLQ-PLALEGSLOKEAEDLQVGQVEL GGGPGAGSLQPLA-LEGSLQK (SEQ ID NO: 8).

The fusion protein in protocol 3 was substantially identical to that in example 1, except for n=4.

The result showed that the amount of target product produced by protocol 2 was too small to detect. This demonstrated that the upstream peptide of 6His and the linker peptide formed a conformation facilitating high efficient expression and secretion. The desired expression protein was obtained by protocol 3.

Example 4

*Pichia pastoris* Expressing the Fusion Protein of Human Proinsulin C-Peptide—Construction of Engineered Cells Suitable expression vector and host bacterium system were selected: expression vector plasmid pET-30a(+) was obtained from Novagen and the recipient bacterium was *E. coli* BL21 (DE3).

The gene sequence of the fusion protein in example 1 was examined not to contain any rare codon for *E. coli*. The gene was cloned into pUC19, verified by sequencing and cloned into the expression vector pET-30a(+). After it was confirmed by sequencing that no frame change had occurred, the vector was transformed into *E. coli* BL21(DE3), thereby obtaining the engineering bacteria.

Figure 3:
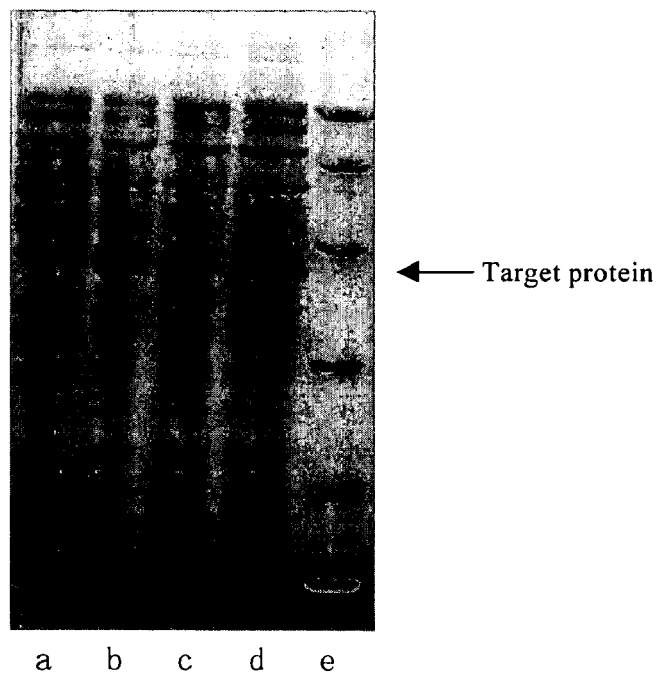
FIG. 3 shows the SDS-PAGE electrophoresis analysis of fusion protein of human proinsulin C-peptide expressed by *E. coli* (shake flask characterization). Lanes a, b, c and d: induction for 0 h, 1 h, 2 h, and 3 h, respectively (the contents of the target protein are 0%, 11.47%, 11.88%, and 12.36%, respectively); e: molecular weight standards (from top to bottom, molecular weights are 96 KD, 66 KD, 43 KD, 31 KD, 20.1 KD, and 14.4 KD)

The verified engineering bacteria were seeded into 10 mL LB medium (the concentration of kanamycin: 100 μg/mL), cultured under 37° C., 250 rpm to an $OD_{600}$=0.5-1.0 when cells were in the log growth phase. IPTG was added under sterilized condition to a final concentration of 1 mM and the induction of expression was continued under 37° C., 250 rpm. Samples were taken after 3 hours, and the expression of the target protein was determined by SDS-PAGE, which showed a band at the position of 41 KD (FIG. 3).

Example 5

The Pilot-Plant Fermentation Of Pichia *pastoris* For Expression Of The Fusion Protein Of Human Proinsulin C-Peptide The *Pichia pastoris* engineered cells obtained from example 1 were fermented with the following methods:
NBS BioFlo 3000 Fermenter (5 L):
1. Seed liquid: BMGY Medium
2. Fermentation medium: low salt fermentation medium
3. Incubation period of fermentation:
Temperature: 30° C.
PH: 5.0
DO: ≧30%
Wet cell weight before methanol induction: 88 g/L
4. Induction period of Fermentation:
Temperature: 30° C.
pH: 6.5
DO: ≧20%
$PTM_1$ content in methanol supplement: 10 ml/L
Wet cell weight after methanol induction: 257 g/L
In the late stage of the incubation period, methanol was added by flowing after glycerol was exhausted for the purpose of induction, and the methanol concentration was maintained at 0.5-1% during the whole induction period of 20-50 hours.

Figure 4:
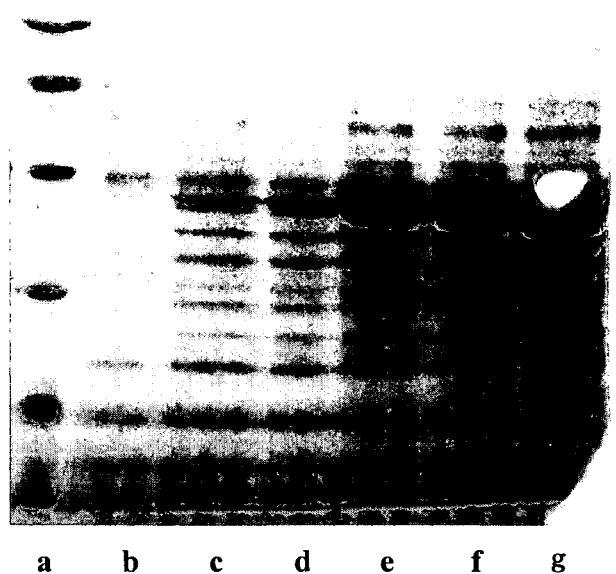
FIG. 4 shows the SDS-PAGE electrophoresis analysis of fusion protein of human proinsulin C-peptide from Pichia *pastoris* fermentation. Lane a: molecular weight standards (from top to bottom, molecular weights are 96 KD, 66 KD, 43 KD, 31 KD, 20.1 KD, and 14.4 KD); b: before induction; c-g: Induction for 8, 16, 24, 32 and 48 h.

After 48 hours of induction, the fusion protein of human proinsulin C-peptide accounted for 47% of total proteins in the fermentation supernatant, with the expression level reaching 1 mg/ml (measured by improved Lowry method) (FIG. 4).

Example 6

The Pilot-Plant Fermentation of *E. coli* for Expression of the Fusion Protein of Human Proinsulin C-Peptide The *E. coli* engineered cells obtained in example 4 were fermented with the following method:
NBS BioFlo 3000 Fermenter (5 L):
1. Seed liquid: LB Medium
2. Fermentation medium: M9 medium (3.5 L)
3. Incubation period of fermentation:
Temperature: 37° C.
pH: 7.0
DO: 80%
$OD_{600}$ before induction: 1.52
4. Induction period of fermentation:
Temperature: 35° C.
pH: 6.5
DO: 50%
Content of trace element solution (PTM) in glucose supplement: 10 ml/L
$OD_{600}$ after IPTG induction: 5.72
In the late stage of the incubation period, when $OD_{600}$ increased to about 1.5, IPTG was added at one time to the final concentration of 1 mM to induce expression. Glucose supplement was added by flowing during the whole process of induction to maintain pH in the range of 6.9-7.2. Induction time was 3 hours.

Figure 5:
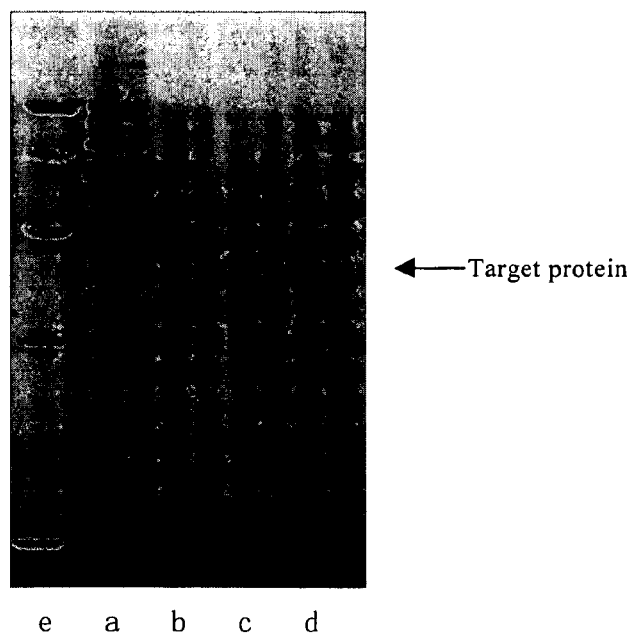
FIG. 5 shows the SDS-PAGE electrophoresis analysis of fusion protein of human proinsulin C-peptide from *E. coli* fermentation. Lanes a, b, c and d: induction for 0 h, 1 h, 2 h, and 3 h, respectively (The contents of the target protein are 0%, 24.87%, 27.89%, and 30.33%, respectively); e: molecular weight standards (from top to bottom, molecular weights are 96 KD, 66 KD, 43 KD, 31 KD, 20.1 KD, and 14.4 KD).

After 3 hours of induction, 25.7 g bacteria were obtained by centrifugation. The fusion protein of human proinsulin C-peptide accounted for 35% of the total proteins in the fermentation bacteria, with the protein content reaching 1.02 mg/ml (measured by improved Lowry method). The total amount of target protein was 1.25 g, and the expression level reached 0.357 g/L of the fermentation medium (FIG. 5).

Example 7

Pichia *pastoris* Expresses the Fusion Protein of Human Proinsulin C-Peptide-Enzymatic Digestion After preliminary purification, the resultant expression supernatant of *Pichia pastoris* engineered cells from example 5 was subjected to one-step enzymatic digestion. The conditions for enzymatic digestion were as follows:
Enzymes: TPCK-Trypsinase (Sigma), carboxypeptidase B (Sigma)
Buffer: 10 mM PB (pH7.4)
The ratio of C-peptide fusion protein to TPCK-Trypsinase was 200: 1(W/W)
The ratio of C-peptide fusion protein to carboxypeptidase B was 200: 1(W/W)
Temperature for enzymatic digestion: 25° C.
Time for enzymatic digestion: 6 h.
After enzymatic digestion, the resultant C-peptide was subjected to HPLC analysis. The conditions for HPLC analysis were as follows:
C18 analysis column Φ4.6*250 mm
λ: 230 nm
Buffer A: 0.1% TFA buffer B: 0.08% TFA 70% acetonitrile

| Gradient: | 0-5 min | 0% buffer B |
| --- | --- | --- |
| | 5-10 min | 30% buffer B |
| | 10-30 min | 60% buffer B |
| | 30-31 min | 100% buffer B |

Figure 6:
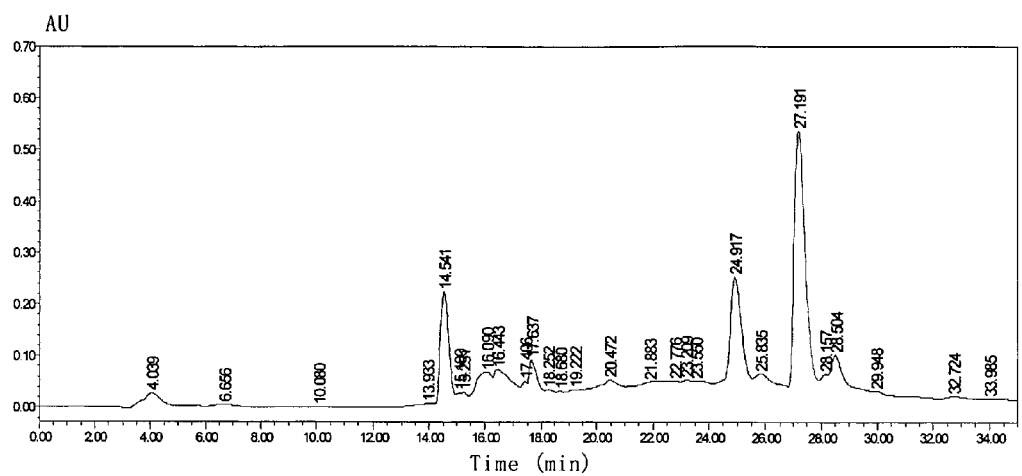
FIG. 6 shows the result of HPLC analysis for the C-peptide after enzymatic digestion.

As illustrated in FIG. 6, the retention time for the primary products of enzymatic digestion was 27±1 min in accordance with the retention time of C-peptide monomer, indicating that the C-peptide monomers were produced after enzymatic digestion.

Example 8

Purification of Enzymatic Digestion Products

The enzymatic digestion products of example 7 were subjected to purification, the specific conditions employed were as follows:
Chromatography media: Q-Sepharose FF (Pharmacia)
buffer A: 10 mM PB buffer B: 10 mMPB+1M NaCl
Gradient: 0-100% buffer B 20 column volume
Flowing rate: 60 cm/h The digestion products obtained in example 7 were subjected to ultrafiltration or dialysis to remove the salts and some impurities. Then, the sample was loaded onto the column; rinsed with buffer A till UV baseline became stable. Then, linear gradient was employed, in which 20CV was used to establish the B % from 0 to 100. The sample appeared at the concentration of about 20% B. The sample was collectedwith individual tubes. The recovery rate of the sample was above 60%, with the purity over 95%.

Figure 7:
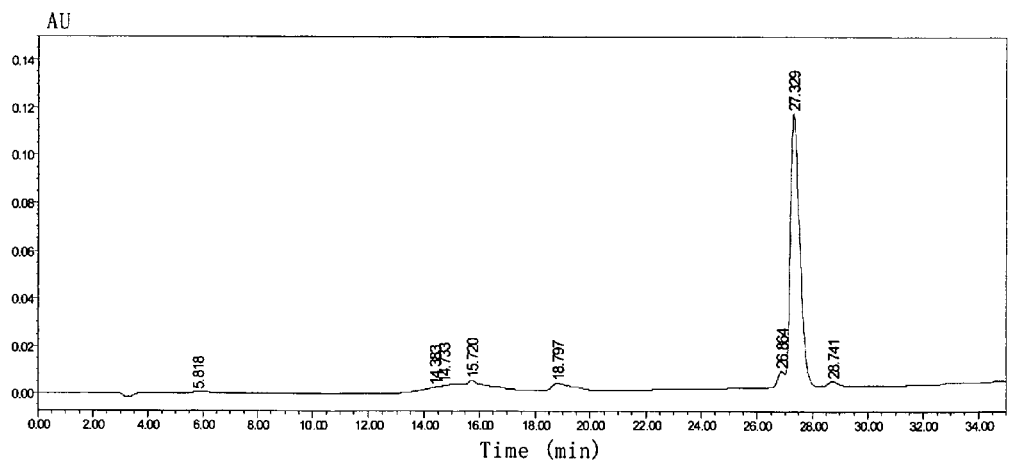
FIG. 7 shows the result of HPLC analysis for the C-peptide after purification.

Since the sample had a high content of salts, the collected sample was subjected to desalting treatment with G-50 Sephadex using buffer A as the desalting buffer. The recovery rate of the sample was above 90%, with the HPLC purity over 98% (FIG. 7).

The sequence of the sample was confirmed to be entirely identical to that of the natural human proinsulin C-peptide, so that the product was verified to be human proinsulin C-peptide.

Example 9

Preparation of the Purified Product

10% mannitol was added into the purified original stock solution obtained in Example 8. The resultant product was subpackaged and lyophilized to form the powder preparation of the C-peptide for injection. Its stability was proved by stability test. Activity assay demonstrated that human proinsulin C-peptide prepared with the methods of the present invention had the same activity as that of the standard sample.

INDUSTRIAL PRACTICABILITY

Based on the disclosure aforementioned, the advantages of expressing the fusion protein of invention by such expression systems as Pichia pastoris include high expression level, high stability, and convenience to obtain the C-peptide or other short peptide monomers by simple enzymatic digestion and separation of the obtained fusion protein. The method of the present invention significantly reduces the complexity of the whole process and highly increases the productivity, which is particularly suitable for the large-scale production of the short peptides such as the C-peptide.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

What is claimed is:

1. A fusion protein having the following structure:

X1-C1-Lys-(X2-C2-Lys)n-X3 wherein
X1 is MHHHHHHRSK (SEQ ID NO:4);
C1 and C2 human proinsulin C-peptides;
X2 is AGSK (SEQ ID NO:5);
X3 is a downstream peptide of 3-15 amino acids in length, and the first three amino acids thereof are AGS; and
n is an integer of 3-30.

2. The protein according to claim 1 wherein the protein has the amino acid sequence as shown in SEQ ID NOs: 2 or 3.

3. A method for producing peptides comprising:
(a) digesting the fusion protein of claim 1 with trypsinase and carboxypeptidase B, thereby forming peptides C1 and C2; and
(b) isolating peptides C1 and C2.

* * * * *